United States Patent
Hammer

(10) Patent No.: US 9,726,395 B2
(45) Date of Patent: Aug. 8, 2017

(54) AIR FRESHENING SYSTEM AND METHOD

(71) Applicant: Scott David Hammer, Dallas, TX (US)

(72) Inventor: Scott David Hammer, Dallas, TX (US)

(*) Notice: Subject to any disclaimer, the term of this patent is extended or adjusted under 35 U.S.C. 154(b) by 583 days.

(21) Appl. No.: 13/843,232

(22) Filed: Mar. 15, 2013

(65) Prior Publication Data

US 2014/0141709 A1     May 22, 2014

Related U.S. Application Data

(60) Provisional application No. 61/728,603, filed on Nov. 20, 2012.

(51) Int. Cl.
| | |
|---|---|
| *F24F 13/08* | (2006.01) |
| *A61L 9/12* | (2006.01) |
| *F24F 13/28* | (2006.01) |
| *A61L 9/04* | (2006.01) |
| *F24F 3/16* | (2006.01) |

(52) U.S. Cl.
CPC ............ *F24F 13/082* (2013.01); *A61L 9/048* (2013.01); *A61L 9/12* (2013.01); *A61L 2209/14* (2013.01); *A61L 2209/16* (2013.01); *F24F 2003/1689* (2013.01); *Y10T 29/49947* (2015.01); *Y10T 29/49948* (2015.01)

(58) Field of Classification Search
None
See application file for complete search history.

(56) References Cited

U.S. PATENT DOCUMENTS

| | | | | |
|---|---|---|---|---|
| 4,903,584 A | * | 2/1990 | Styles | A61L 9/12 239/57 |
| 5,141,707 A | * | 8/1992 | Brite | 422/124 |
| 5,240,487 A | * | 8/1993 | Kung | 96/222 |
| 5,240,653 A | | 8/1993 | Ramkissoon | |
| 5,273,690 A | * | 12/1993 | McDowell | 261/107 |
| 5,344,287 A | * | 9/1994 | Schaefer | F04D 29/601 415/213.1 |
| 5,422,078 A | * | 6/1995 | Colon | 422/123 |
| 5,460,787 A | * | 10/1995 | Colon | A61L 9/12 239/55 |
| 5,478,505 A | * | 12/1995 | McElfresh | B60H 3/0007 239/57 |
| 5,525,145 A | * | 6/1996 | Hodge | 96/17 |
| 5,547,636 A | * | 8/1996 | Vick | A61L 9/042 239/60 |
| 5,662,835 A | | 9/1997 | Collingwood | |

(Continued)

OTHER PUBLICATIONS

Felix Buccellato et al., "What Every Marketer Should Know about Fragrance," Oct. 2, 2001, pp. 1-8.

*Primary Examiner* — Eric Gorman
(74) *Attorney, Agent, or Firm* — D. Scott Hemingway; Hemingway & Hansen, LLP

(57) ABSTRACT

The present invention supports an airflow register accessory comprising an accessory having an outer and an inner surface and defining vents, a fastening mechanism located on the inner surface of the accessory, and a scented component located on the inner surface adjacent and accessorizing the vents. In a preferred embodiment, the accessory may be easily attached to and detached from the room-facing surface of an airflow register. Upon air flow from an HVAC system through the airflow register and airflow register accessory, a pleasant scent may be imparted to the room via release of scent from the scented component.

21 Claims, 6 Drawing Sheets

(56) References Cited

U.S. PATENT DOCUMENTS

| | | | |
|---|---|---|---|
| 5,690,719 A * | 11/1997 | Hodge | 96/17 |
| 5,698,166 A * | 12/1997 | Vick | A61L 9/042 |
| | | | 261/30 |
| 5,899,382 A * | 5/1999 | Hayes | A61L 9/12 |
| | | | 239/56 |
| 5,947,815 A | 9/1999 | Danforth | |
| 6,234,893 B1 * | 5/2001 | Meredith | 454/289 |
| 6,241,603 B1 * | 6/2001 | Watson | 454/284 |
| 6,257,976 B1 * | 7/2001 | Richardson, III | 454/309 |
| 6,319,117 B1 * | 11/2001 | Moore | F24F 13/06 |
| | | | 454/328 |
| 6,386,971 B1 * | 5/2002 | Johnson | A61L 9/12 |
| | | | 422/124 |
| 6,569,673 B1 * | 5/2003 | Nakagawa et al. | 435/286.6 |
| 6,749,499 B1 * | 6/2004 | Snyder | 454/289 |
| 6,814,660 B1 * | 11/2004 | Cavett | 454/284 |
| 6,878,057 B1 | 4/2005 | Calloura | |
| 7,007,863 B2 | 3/2006 | Kotary et al. | |
| 7,811,346 B1 * | 10/2010 | Henson | 55/385.1 |
| 8,293,170 B1 * | 10/2012 | Schuld | B01D 46/0005 |
| | | | 239/60 |
| 8,746,587 B2 | 6/2014 | Soldan et al. | |
| 8,765,063 B1 * | 7/2014 | Mazzilli | 422/120 |
| 8,784,524 B2 * | 7/2014 | Albert | 55/373 |
| 8,851,458 B1 * | 10/2014 | Wilson | 261/101 |
| 8,870,995 B1 * | 10/2014 | Bender | 55/508 |
| 2002/0157540 A1 * | 10/2002 | Lynn | 96/222 |
| 2003/0097936 A1 * | 5/2003 | Maleeny | A61L 9/012 |
| | | | 95/285 |
| 2004/0082495 A1 * | 4/2004 | Maleeny et al. | 512/1 |
| 2004/0223891 A1 * | 11/2004 | Brown | 422/124 |
| 2007/0140924 A1 * | 6/2007 | Hill | 422/124 |
| 2007/0199948 A1 * | 8/2007 | Ericson | 220/747 |
| 2008/0083337 A1 * | 4/2008 | Yamanaka | A61L 9/042 |
| | | | 96/222 |
| 2008/0190789 A1 * | 8/2008 | D'Amico | A61L 9/12 |
| | | | 206/229 |
| 2008/0305016 A1 * | 12/2008 | Fernandez Torres | A61L 9/042 |
| | | | 422/123 |
| 2009/0078121 A1 * | 3/2009 | Hepburn | 96/222 |
| 2009/0120291 A1 * | 5/2009 | Hassell et al. | 95/273 |
| 2010/0038443 A1 | 2/2010 | Pankhurst et al. | |
| 2010/0078498 A1 | 4/2010 | Gasper | |
| 2010/0116898 A1 | 5/2010 | Litten-Brown et al. | |
| 2010/0163639 A1 | 7/2010 | Pankhurst et al. | |
| 2010/0187324 A1 | 7/2010 | Feygin et al. | |
| 2010/0227545 A1 * | 9/2010 | Frois | 454/358 |
| 2010/0237162 A1 | 9/2010 | Litten-Brown et al. | |
| 2010/0294852 A1 | 11/2010 | Banco et al. | |
| 2011/0044846 A1 * | 2/2011 | McNally et al. | 422/4 |
| 2011/0204158 A1 | 8/2011 | Saari | |
| 2011/0303757 A1 | 12/2011 | Blondeau et al. | |
| 2012/0024974 A1 | 2/2012 | Grodsky et al. | |
| 2012/0024975 A1 | 2/2012 | Sharma et al. | |
| 2012/0024979 A1 * | 2/2012 | Wadlin | 239/44 |
| 2012/0079945 A1 | 4/2012 | Roberts | |
| 2012/0126024 A1 | 5/2012 | Boyd et al. | |
| 2013/0000489 A1 * | 1/2013 | Lu | B01D 46/0005 |
| | | | 96/222 |
| 2014/0161673 A1 * | 6/2014 | Hammer | 422/124 |
| 2014/0271130 A1 * | 9/2014 | Hammer | 415/116 |
| 2015/0292755 A1 * | 10/2015 | Pickett | F24F 3/166 |
| | | | 96/74 |

* cited by examiner

AIR FRESHENING SYSTEM AND METHOD

RELATED APPLICATION DATA

This application is related to Provisional Patent Application Ser. No. 61/728,603 filed on Nov. 20, 2012, and priority is claimed for this earlier filing. The Provisional Patent Application is incorporated by reference into this utility patent application.

TECHNICAL FIELD

The present invention relates in general to a system and method for providing an accessory for an air conditioning or heating air flow register such as are installed in the ceiling, walls or floors of homes and/or other buildings.

BACKGROUND OF THE INVENTION

Air flow registers allow the flow of heated or cooled air into rooms of homes, offices and other buildings. Generally, such registers are made of metal and have various vents through which air flows. They may have a lever which can regulate the amount of air which flows through a given register.

Various devices have been used in the past to scent the air of a given room or area in a building. However, such devices may require electricity or heat in order to volatilize the scent so that it distributes throughout the area of interest. The problem with prior art systems is the inability to conceivably, effectively, and easily access the airflow passing through the airflow register to scent the air in the room.

SUMMARY OF THE INVENTION

The present invention supports an airflow register accessory comprising an accessory having an outer and an inner surface and defining vents, a fastening mechanism located on the inner surface of the accessory, and a scented component located on the inner surface adjacent and accessorizing the vents. In a preferred embodiment, the accessory may be easily attached to and detached from the room-facing surface of an airflow register. Upon air flow from an HVAC system through the airflow register and airflow register accessory, a pleasant scent may be imparted to the room via release of scent from the scented component.

DETAILED DESCRIPTION

A system providing an airflow register accessory, an accessory aide and method of applying said accessory to an airflow register is herein disclosed.

The airflow register accessory comprises an accessory, a scented fabric, and a fastening mechanism for attaching the accessory to the room-facing side of an airflow register.

Figure 1:
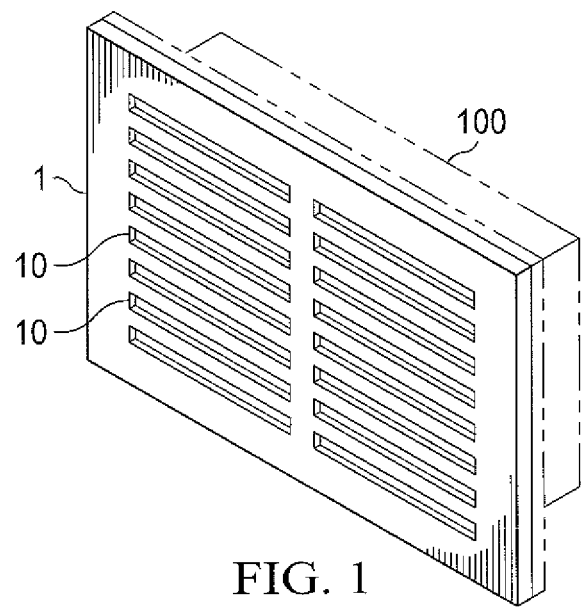
FIG. 1 is a front perspective environmental view illustrating an embodiment of an airflow register accessory in accordance with the principles of the present invention installed on an airflow register (the airflow register which is not part of this invention is shown in phantom throughout the drawings).
Figure 2:
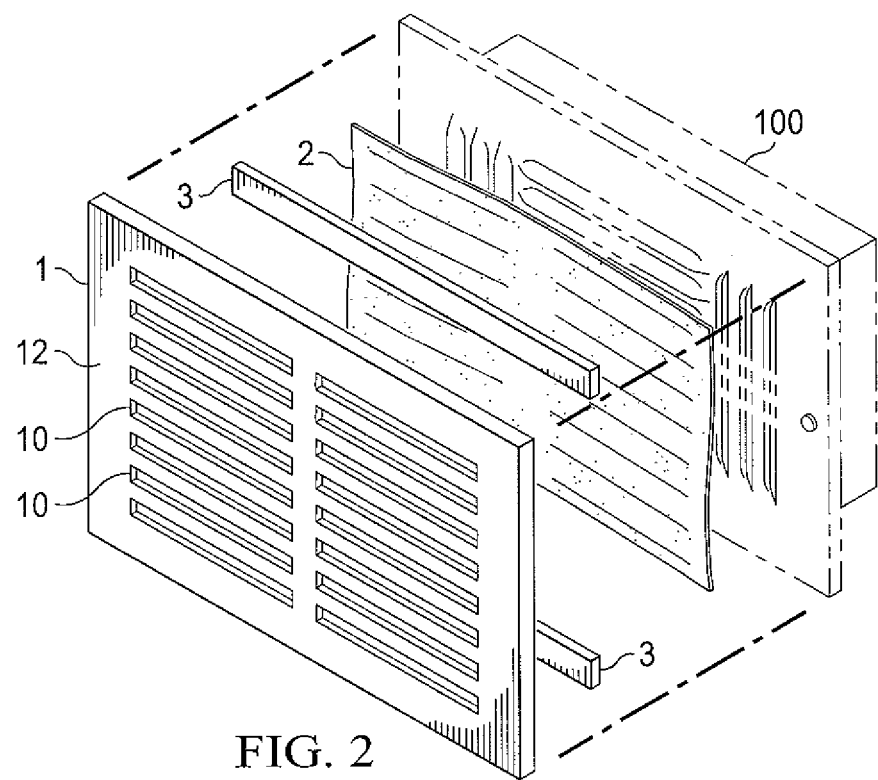
FIG. 2 is an exploded perspective environmental view illustrating an embodiment of an airflow register accessory in accordance with the principles of the present invention in relation to an airflow register, shown in phantom, on which it is installed in use.

As best seen in FIGS. 1 and 2, accessory (1) of the airflow register accessory defines a plurality of vents (10) for air to flow through from the heating, ventilation and air conditioning unit ("HVAC") system of a building, through an airflow register attached to a wall, ceiling or floor of the building, and then though the airflow register accessory of the invention when it is secured to said airflow register (100). FIG. 1 shows the airflow register accessory (1) installed on top over or covering the airflow register (100). Accessory is shown as rectangular, but could be square, circular, or other shapes, which depend on the shape of the air register. A user can also use a larger accessory (example shown in FIG. 10) and move it around as fragrance is dissipated.

FIG. 2 best illustrates the components of the airflow register accessory. The accessory (1) has an outer side (12) and an inner side (13) (not shown in FIG. 2). The airflow register accessory (1) further comprises a fastening mechanism (3) secured to the inner side of the accessory. The fastening mechanism (3) is attached to the inner side of the airflow register accessory (1), and in turn may be used to secure the airflow register accessory to an airflow register (100). Preferably the fastening mechanism (3) are secured to the top and bottom of the inner side (13) to avoid interference with screws, vent levers, and the like of a typical airflow register (100), but may be secured anywhere along the inner side (13) as to allow it to temporarily secure to any type of airflow register.

If the airflow register of interest is metal to which a magnet can adhere, the fastening mechanism can be one or more magnets. This allows for quick and easy attachment or detachment of the airflow register accessory (1) from the airflow register (100) of the room. Magnetic tape strips may also be used. If the accessory is made from non-magnetic material, it is convenient to use a magnetic tape strip that has an adhesive side for adhering to the inner side of the accessory.

Alternatively, other fastening mechanism such as hook and loop fasteners may be employed (not illustrated). In such case, the complement of the hook or the loop is attached to the airflow register (100) and the accessory secured thereto via the complementary fastener (not shown). Double-sided adhesive may also be used to attach the accessory to the airflow register. Less preferred, but possible, are fastening mechanism such as screws or bolts as they can secure the accessory to the airflow register, but make it more arduous to remove and replace the air accessory. If such are used, preferably they will extend through both the airflow register accessory and the airflow register and secure both to the wall, ceiling, or floor.

Figure 5:
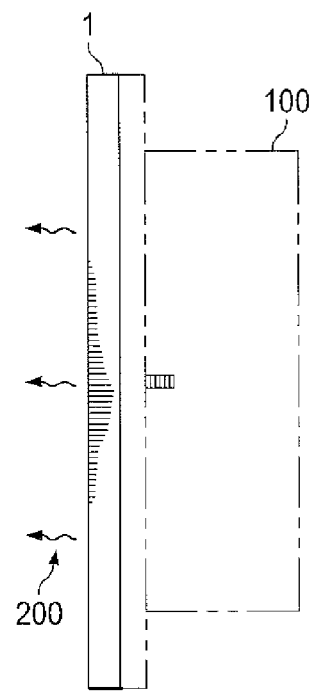
FIG. 5 is a side view of an embodiment of the airflow register accessory as installed on an airflow register (in phantom) with the arrows illustrating air flow direction through the installed airflow register accessory in use.
Figure 6:
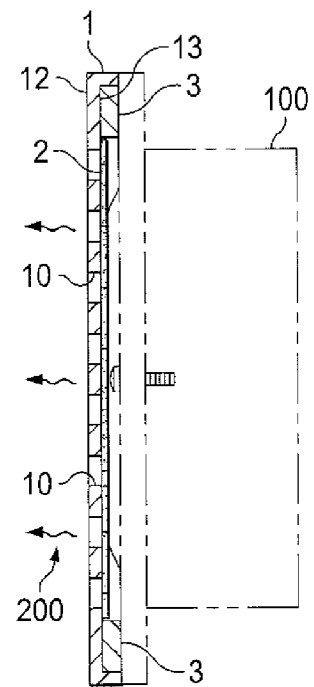
FIG. 6 is a section view along the 6-6 section line of FIG. 3 of an embodiment of the airflow register accessory as installed on an airflow register (in phantom) with the arrows illustrating air flow direction through the installed airflow register accessory in use.

The accessory (1) further comprises a scenting material. FIG. 2 illustrates a scented fabric (2) used for the scenting material. The scented fabric (2) is attached to the inner side (13) of the accessory (1) adjacent the vent openings (10). The scented fabric (2) may be perforated or otherwise woven or spun so that it allows sufficient airflow there through (as illustrated in FIGS. 5 and 6). Alternatively, one or more slits which are oriented in the same way as the vents may be made in the scented fabric (2). The scented fabric (2) may be essentially rectangular to correspond to a rectangular vent area of the accessory, and have four edges—two long and two short. Preferably, at least the short edges are secured by adhesion or other wise to the inside of the accessory (1) so that the scented fabric (2) covers the vent openings (10) of the accessory (1). Airflow register accessory and/or scented fabric may also be other shapes to correspond to size and shape of the airflow register.

Preferably, the scented fabric comprises a substrate which may be made of natural fibers, synthetic fibers, or a mixture of natural fiber and synthetic fibers. Exemplary natural fibers that can be used to form the substrate include wood fibers and non-wood natural fibers such as vegetable fibers, cotton, straw, canes, silk, animal fiber, grasses, hemp, and corn stalks. Nonwoven fabrics are broadly defined as sheet or web structures bonded together by entangling fiber or filaments (and by perforating films) mechanically, thermally or chemically. They are typically flat, porous sheets that are made directly from separate fibers or from molten plastic or plastic film. Some examples of nonwoven materials are staple nonwovens, spun laid nonwovens, and air-laid paper. Woven fabric is a cloth formed by weaving. Synthetic fibers may include a variety of substrates known in the art. An exemplary fiber is polylactide fiber or PLA. PLA is a biodegradable thermoplastic derived from lactic acid.

The fabric material has a weight of approximately 0.2 to 2.0 oz/ft$^2$, but can have weights that vary from 0.05 to 4.55 oz/ft$^2$. An exemplary combination substrate for the fabric comprises a mixture of 0.1 wt. % to 1.00 wt. % of the polylactide fiber and about 10 wt. % to about 1.00 wt. % of the natural fiber. The fabric preferably is flame retardant, and can be composed of a polyester or natural material (woven or non-woven). The airflow rate should be extremely high on the order a thin mesh that freely allows airflow. The fabric component has a high degree of air permeability on the order of not impeding airflow by more than 5% to 10% by uncovered air flow rates.

The scented fabric component is preferably thin, but must be sturdy enough to withstand typical ventilation flows of HVAC systems without being torn or compromised such that it cannot perform the intended function. The ventilation rate is normally expressed by the volumetric flow rate of outside air being introduced to the HVAC. The typical units used are cubic feet per minute (CFM) or liters per second (L/s). The ventilation rate can also be expressed on a per person or per unit floor area basis, such as CFM/p or CFM/ft$^2$.

For residential housing, which mostly relies on air infiltration for ventilation, the common ventilation rate measure is the number of times the whole interior volume of air is replaced per hour, and is called air changes per hour (I or ACH; units of 1/h). During the winter, ACH may range from 0.50 to 0.41 in a tightly insulated house to 1.11 to 1.47 in a loosely insulated house.

The scenting fabric (2) has an air freshening agent loaded thereon. The air freshening agent must be able to adhere to the fabric but at least a portion thereof should be released when air flows through the scented fabric component. In the natural operation of the HVAC system, heated or cooled air will flow through the scenting material. Thus the air freshening agent may be chosen to release when air of any temperature flows through the scenting material at a pre-determined rate, when air having a temperature above a certain threshold (heater in operation) flows through at a pre-determined rate, or when air having a temperature below a certain threshold flows through (air conditioner in operation) flows through at a pre-determined rate. Sufficient air freshening agent should continue to adhere to the scenting fabric so that the air freshening accessory can provide air freshening benefits for a pre-determined period of time. After the pre-determined period of time, it is contemplated that the airflow register accessory will be replaced. Alternatively, but less preferred, only the scented fabric component may be replaced.

A scented strip may be used instead of the scented fabric (2). The scented strip would comprise an adhesive surface that is secured to the inner surface (13) of accessory (1). The scented strip would also comprise a scented surface that is impregnated with a fragrance. Preferably the scented surface has a covering that maintains the fragrance. The fragrance would be activated when the covering is removed. For example, the covering may me a plastic coating or sheet that peels off. The fragrance may be gel-based or oil-based. Preferably a fragrance that is long-lasting and safe to use indoors.

The embodiment of FIG. 2 may also comprise an air filter. The air filter preferably would lie adjacent the surface of the scented fabric (2) opposite the inner surface (13) of accessory (1). The air filter may also lie between the inner surface (13) and scented fabric (2). The air filter would preferably be secured to the accessory (1) by the same method used to secure the scented fabric (2), but other methods may be used that maintain the air filter in place. Additionally, the scented fabric (2) and air filter may be fabricated into a single combined piece. If fabricated into a single combined piece, the single combined piece would be secured to the accessory (1) by the means stated above regarding the scented fabric (2). Any type of air filter may be used as long as it fits inside the accessory and doesn't impede the attachment of the accessory to the air register. Some examples of air filters are fiberglass filters, HEPA filters or washable air filters. Some filters like polyester and pleated filters may not be suitable as they typically have a higher resistance to air flow.

Figure 3:
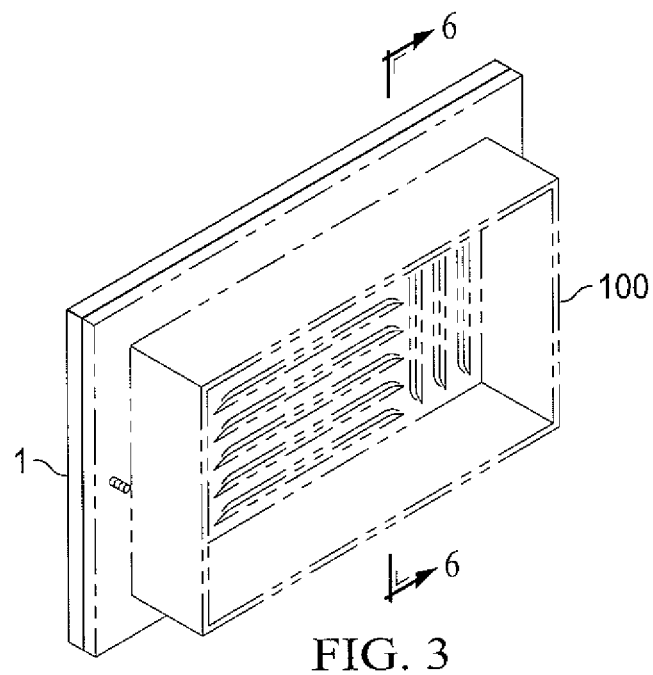
FIG. 3 is a back view illustrating the airflow register accessory installed on an airflow register, shown in phantom.

FIG. 3 illustrates a rear perspective view of a typical airflow register (100) with the accessory (1) secured flush with the airflow register (100). FIG. 3 shows the airflow register accessory (1) installed on top over or covering the airflow register. Accessory is shown as rectangular, but could be square, circular, or other shapes, which depend on the shape of the air register. A user can also use a larger accessory (example shown in FIG. 10) and move it around as fragrance is dissipated.

Figure 4:
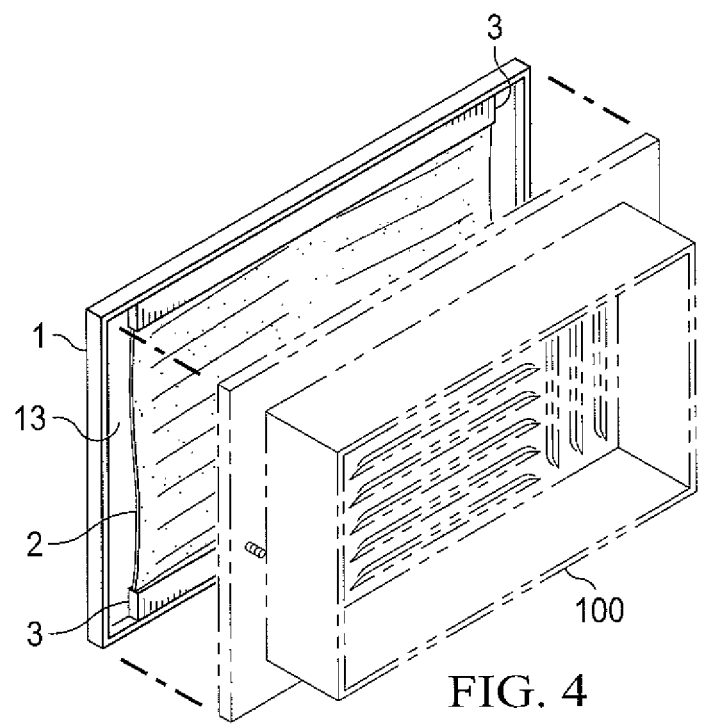
FIG. 4 is a back exploded perspective view of an embodiment of the airflow register accessory in accordance with the principles of the present invention in relation to an airflow register, shown in phantom, on which it is installed in use.

FIG. 4 also illustrates the components of the airflow register accessory of FIG. 2. The accessory (1) has an outer side (not shown in FIG. 4) and an inner side (13). The airflow register accessory (1) further comprises a fastening mechanism (3) secured to the inner side of the accessory. The fastening mechanism (3) is attached to the inner side (13) of the airflow register accessory (1), and in turn may be used to secure the airflow register accessory to an airflow register (100). Preferably the fastening mechanism (3) are secured to the top and bottom of the inner side (13) to avoid interference with screws, vent levers, and the like of a typical airflow register (100), but may be secured anywhere along the inner side (13) as to allow it to temporarily secure to any type of airflow register.

If the airflow register of interest is metal to which a magnet can adhere, the fastening mechanism can be one or more magnets. This allows for quick and easy attachment or detachment of the airflow register accessory (1) from the airflow register (100) of the room. Magnetic tape strips may also be used. If the accessory is made from non-magnetic material, it is convenient to use a magnetic tape strip that has an adhesive side for adhering to the inner side of the accessory.

Other fastening mechanisms such as hook and loop fasteners may be employed (not illustrated). In such case, the complement of the hook or the loop is attached to the airflow register (100) and the accessory secured thereto via the complementary fastener (not shown). Double-sided adhesive may also be used to attach the accessory to the airflow register. Less preferred, but possible, are fastening mechanism such as screws or bolts as they can secure the accessory to the airflow register, but make it more arduous to remove and replace the air accessory. If such are used, preferably they will extend through both the airflow register accessory and the airflow register and secure both to the wall, ceiling, or floor.

Alternatively, accessory (1) may comprise attachment extensions that extend inward from the inner surface (13). Fastening mechanisms (3) would be secured to the attachment mechanisms. By providing the attachment extensions, the thickness of the accessory may be varied and allow the same fastening mechanisms to be used. The extensions may also be cost effective as it allows for thinner fastening mechanisms to be used.

The accessory (1) further comprises a scenting material. FIG. 4 illustrates a scented fabric (2) used for the scenting material. The scented fabric (2) is attached to the inner side (13) of the accessory (1) adjacent the vent openings (10). The scented fabric (2) may be perforated or otherwise woven or spun so that it allows sufficient airflow therethrough (as illustrated in FIGS. 5 and 6). Alternatively, one or more slits which are oriented in the same way as the vents may be made in the scented fabric (2).

The scented fabric (2) may be essentially rectangular to correspond to a rectangular vent area of the accessory, and have four edges—two long and two short. Preferably, at least the short edges are secured by adhesion or other wise to the inside of the accessory (1) so that the scented fabric (2) covers the vent openings (10) of the accessory (1). Airflow register accessory and/or scented fabric may also be other shapes to correspond to size and shape of the airflow register.

The scenting fabric (2) has an air freshening agent loaded thereon, which is a scented oil or additive. The scented additive can include an essential oil or concentrated additive containing a concentrated fragrance or scent. When disposed on the fabric the scented additive is diluted with a water-based diluent up to 80% to 90% (or over) per weight of the scented additive. The diluent evaporates after application leaving the scented additive on the scented fabric (2) of the airflow register. The air freshening agent must be able to adhere to the fabric but at least a portion thereof should be released when air flows through the scented fabric component. In the natural operation of the HVAC system, heated or cooled air will flow through the scenting material. Thus the air freshening agent may be chosen to release when air of any temperature flows through the scenting material at a pre-determined rate, when air having a temperature above a certain threshold (heater in operation) flows through at a pre-determined rate, or when air having a temperature below a certain threshold flows through (air conditioner in operation) flows through at a pre-determined rate. Sufficient air freshening agent should continue to adhere to the scenting fabric so that the air freshening accessory can provide air freshening benefits for a pre-determined period of time. After the pre-determined period of time, it is contemplated that the airflow register accessory will be replaced. Alternatively, but less preferred, only the scented fabric component may be replaced.

A scented strip may be used instead of the scented fabric (2). The scented strip would comprise an adhesive surface that is secured to the inner surface (13) of accessory (1). The scented strip would also comprise a scented surface that is impregnated with a fragrance. Preferably the scented surface has a covering that maintains the fragrance. The fragrance would be activated when the covering is removed. For example, the covering may me a plastic coating or sheet that peels off. The fragrance may be gel-based or oil-based. Preferably a fragrance that is long-lasting and safe to use indoors.

The embodiment of FIG. 4 may also comprise an air filter. The air filter preferably would lie adjacent the surface of the scented fabric (2) opposite the inner surface (13) of accessory (1). The air filter may also lie between the inner surface (13) and scented fabric (2). The air filter would preferably be secured to the accessory (1) by the same method used to secure the scented fabric (2), but other methods may be used that maintain the air filter in place. Additionally, the scented fabric (2) and air filter may be fabricated into a single combined piece. If fabricated into a single combined piece, the single combined piece would be secured to the accessory (1) by the means stated above regarding the scented fabric (2). Any type of air filter may be used as long as it fits inside the accessory and doesn't impede the attachment of the accessory to the air register. Some examples of air filters are fiberglass filters, HEPA filters or washable air filters. Some filters like polyester and pleated filters may not be suitable as they typically have a higher resistance to air flow.

FIG. 5 best illustrates the side view of the airflow register accessory attached to an airflow register in use. FIG. 5 shows the airflow register accessory (1) installed on top over or covering the airflow register (100). Preferably the accessory back lays flush with the airflow register's front surface. This allows the accessory to appear as part of the register and more natural.

FIG. 6 is a cross-section taken along the section line 6-6 of FIG. 3 where the airflow register accessory (1) is installed on top over or covering the airflow register (100). In a preferred embodiment, the airflow register accessory (1) adheres to the airflow register via magnetic attraction. The room constantly has a pleasant scent for a period of time from the HVAC system causing airflow (200) through the airflow register (100) and through the airflow register accessory (1) adhered thereto. When the scent diminishes or no longer is evident, the airflow register accessory may be replaced as a unit. Accessory (1) of the airflow register accessory defines a plurality of vents (10) for air to flow through from the heating, ventilation and air conditioning unit ("HVAC") system of a building, through an airflow register attached to a wall, ceiling or floor of the building, and then though the airflow register accessory of the invention when it is secured to said airflow register (100). Accessory (1) is shown as rectangular, but could be square, circular, or other shapes, which depend on the shape of the air register. A user can also use a larger accessory (example shown in FIG. 10) and move it around as fragrance is dissipated.

Figure 7:
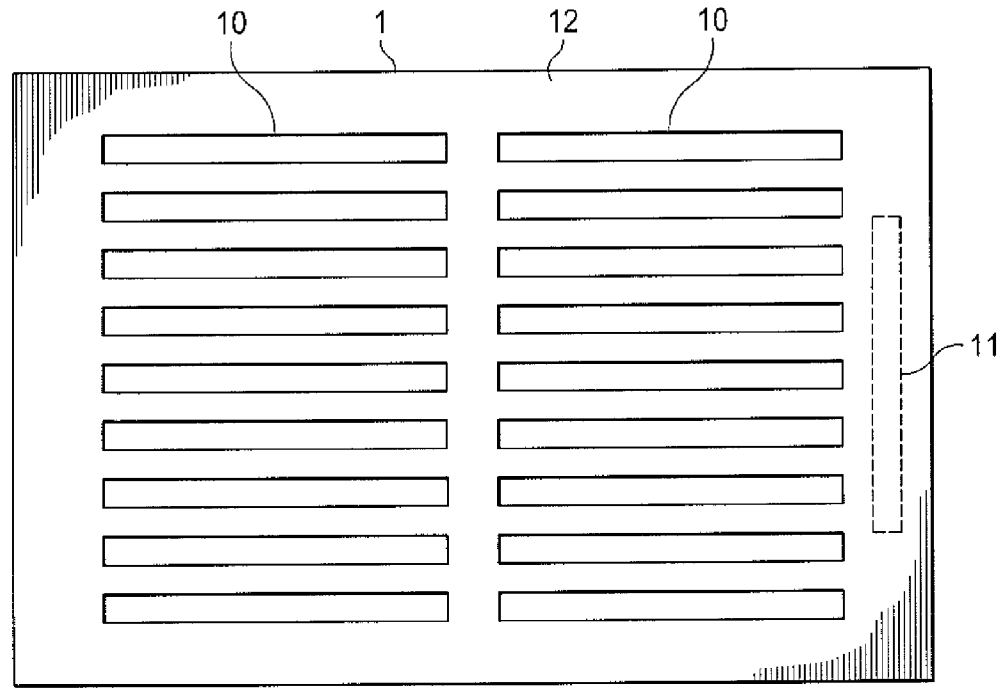
FIG. 7 is a front view of an embodiment of the airflow register accessory illustrating an optional perforated slot portion.

As illustrated in FIG. 7, accessory (1) may further define a perforated slot portion (11). The perforated slot portion (11) may optionally be removed from the airflow register accessory; thereby creating a slot through which an airflow register's regulating lever may pass through, if the airflow register has such a lever. The perforated slot portion (11) may be punched out by hand pressure or by using an implement to push it out, such as a common screwdriver.

Figure 8:
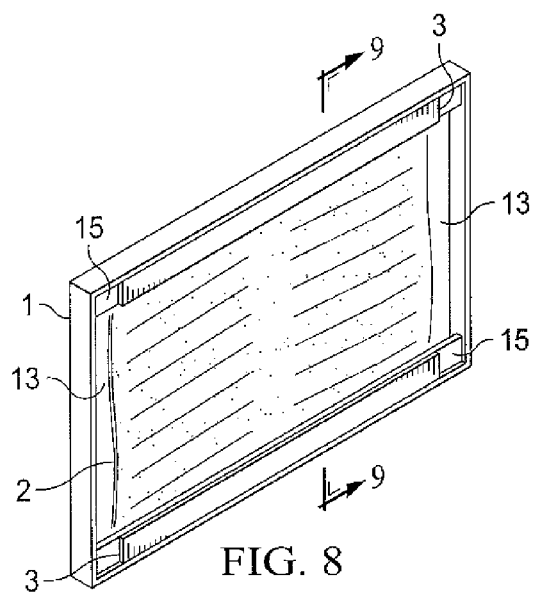
FIG. 8 is a rear perspective view illustrating another embodiment of an airflow register accessory in accordance with the principles of the present invention.

FIG. 8 illustrates an alternate embodiment for the airflow register accessory. This embodiment of the accessory (1) comprises a spacing wall (15). The spacing wall (15) is a thin strip extending inward perpendicularly from the accessory side wall and extending parallel to the accessory front wall a distance from the inner side (13).

Figure 9:
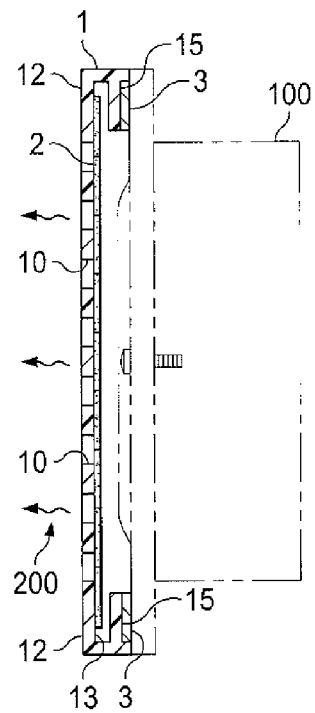
FIG. 9 is a section view along the 9-9 section line of FIG. 8 of the embodiment of the airflow register accessory as installed on an airflow register (in phantom) with the arrows illustrating air flow direction through the installed airflow register accessory in use.

FIG. 9 is a section view along section line 9-9 of FIG. 8 that further illustrates the alternate embodiment of FIG. 8. The spacing wall (15) is preferably located a slight distance away from the accessory back edge as to allow clearance for the securing mechanism (3) to attach thereto and retain the flush securement of the accessory to the airflow register as shown in FIG. 5. The spacing wall (15) also provides more space between the spacing wall (15) and inner side (13) to secure the scenting material (2) to the accessory (1). Another advantage to the spacing wall (15) is that it helps reduce the width of the securing mechanism (3) and may reduce the weight of the accessory (1) to provide easier handling of the accessory (1).

Figure 10:
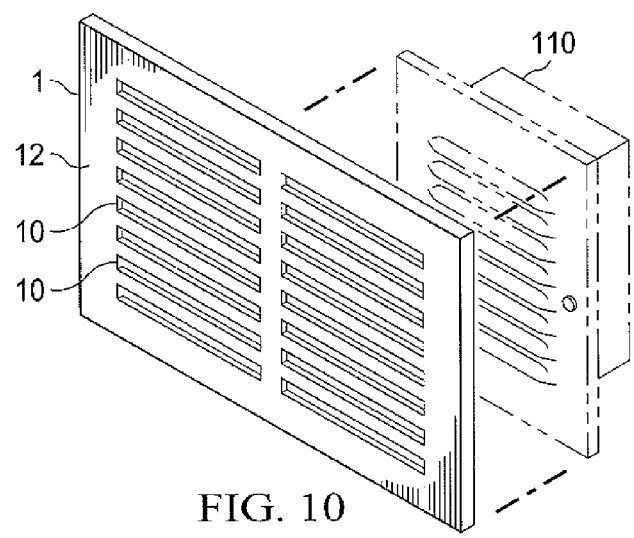
FIG. 10 is a partial exploded perspective environmental view illustrating an embodiment of an airflow register accessory in accordance with the principles of the present invention in relation to an airflow register of differing size, shown in phantom, on which it is installed in use.

As airflow registers may vary in size and shape, the airflow register accessory (1) may also be created in various sizes. For example, as illustrated in FIG. 10, a user may use a larger accessory with a smaller airflow register (110). This configuration may allow the accessory to last longer as less of the scenting material area is used, allowing the user to later adjust the accessory to use the remaining scenting material.

Figure 11:
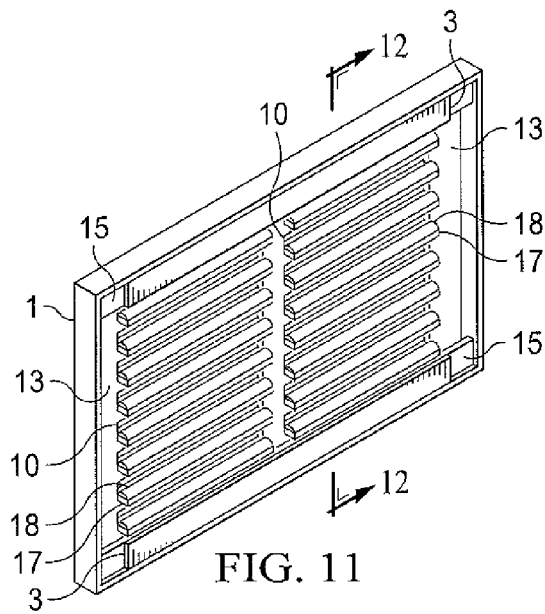
FIG. 11 is a rear perspective view illustrating another embodiment of an airflow register accessory in accordance with the principles of the present invention.

FIG. 11 illustrates another alternate embodiment of the airflow register accessory. The embodiment is similar to the embodiment described above in FIG. 4 with an alteration to the scenting material. In lieu of a scented fabric, the embodiment of FIG. 11 employs a scented gel (18). The inner side (13) of accessory (1) comprises multiple inner ledges (17) that extend out from the inner side surface. The inner ledges (17) each have four edges, two long and two short. One of the long edges is secured to or extends from a long edge of vent opening (10) providing the inner ledge (17) with a surface adjacent the vent opening (10) and a surface adjacent the inner side (13). On the surface adjacent the vent opening (10), the inner ledge (17) comprises a scented gel (18) secured thereto which acts as the air freshening agent.

A scented strip may be used instead of the scented gel (18). The scented strip would comprise an adhesive surface that is secured to the inner surface (13) of accessory (1) or secured to the inner ledge (17) on the surface adjacent the vent opening (10). The scented strip would also comprise a scented surface that is impregnated with a fragrance. Preferably the scented surface has a covering that maintains the fragrance. The fragrance would be activated when the covering is removed. For example, the covering may me a plastic coating or sheet that peels off. The fragrance may be gel-based or oil-based. Preferably a fragrance that is long-lasting and safe to use indoors.

The embodiment of FIG. 11 may also comprise an air filter. The air filter would preferably lie adjacent the long non-secured edges of inner ledges (17). The air filter would preferably be secured to the accessory (1) by tape, glue or adhesive, but other methods may be used that maintain the air filter in place. Any type of air filter may be used as long as it fits inside the accessory and doesn't impede the attachment of the accessory to the air register. Some examples of air filters are fiberglass filters, HEPA filters or washable air filters. Some filters like polyester and pleated filters may not be suitable as they typically have a higher resistance to air flow.

Figure 12:
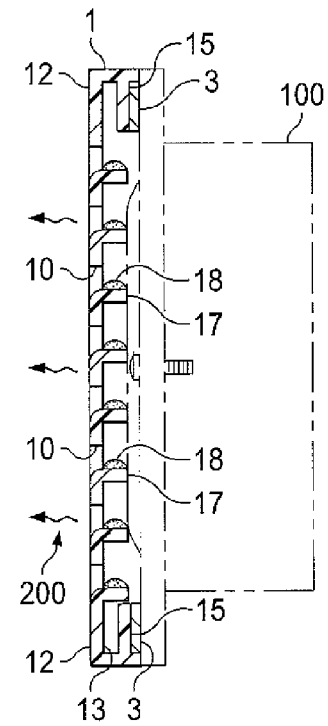
FIG. 12 is a section view along the 12-12 section line of FIG. 11 of the embodiment of the airflow register accessory as installed on an airflow register (in phantom) with the arrows illustrating air flow direction through the installed airflow register accessory in use.

FIG. 12 further illustrates the embodiment shown in FIG. 11. FIG. 12 shows inner ledges (17) and scented gel (18) residing in front of the airflow register (100) when airflow register accessory (1) is attached to the airflow register (100). The airflow (200) flows out of the airflow register (100) passes along the scented gel (18) residing on the inner ledges (17), through vent openings (10) and out to the room.

The scented gel is preferably a polymeric, polyester, gelatin, polysaccharide gel or a glycol base element ranging in 50% to 70% by weight of the gel composition. The properties of the gel range from free-flowing liquids to liquid gels and self-supporting solid gels with a wide range of textures, setting temperatures and melting temperatures. Preferably the gel is self supporting gel so that it remains in the location it is applied on the device despite movement or rotation of the device. The gel composition is dilute when applied, but firms significantly after application to the airflow register. The gel when applied to the airflow register has a diluent of water in the range of 30% to 50% by weight of the gel composition, and includes anti-microbial additives to prevent microbial contamination and growth in the range of 0.20% to 5% of weight of the gel composition.

The gel composition has a scented fragrance component in the overall range of 0.75% to 3.75% by weight of the gel composition, and a colorant of 0.05% to 2.75% by weight of the gel composition.

The gel composition may also be composed of a viscoelastic gel having carrageenan and selected polymers, each polymer having either a cationic nitrogen content of at least about 3 wt. % and a weight average molecular weight of less than about 800,000 Dalton, and is selected from the group consisting of poly(diallyldimethyl ammonium halide), poly(DADMAC), and combinations thereof, or a cationic nitrogen content of less than about 3 wt. % and a weight average molecular weight of greater than about 1,000,000 Dalton. The polymer may be selected from cationic guar gum, a cationic cellulose, a cationic starch, hydrophobically-modified versions thereof, and combinations thereof.

These properties allow the gel to continuously release a scented aroma over an extended period of time. As with the other embodiments, it is contemplated that the airflow register accessory will be replaced once the air freshening agent has dissipated.

Figure 13:
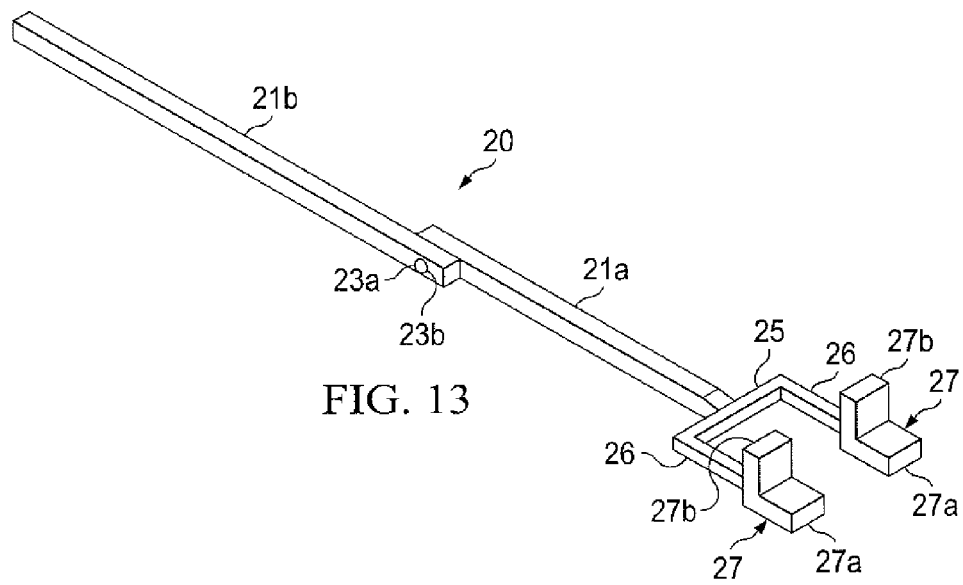
FIG. 13 illustrates an accessory aide in accordance with the principles of the present invention.

In addition to the airflow register accessory (1), the system of the invention comprises an accessory aide (20) as shown in FIG. 13. The accessory aide (20) comprises an upper portion (21a) and a lower portion (21b). The upper portion (21a) further comprises a holding section (25) at one of its ends. At the opposite end the holding section (25) on upper portion (21a) extends an attaching extension (23a) perpendicular to the upper portion (21a). Lower portion (21b) defines an attaching aperture (23b) at one of its ends. The attaching aperture (23b) is complimentary to the attaching extension (23a). The attaching extension (23a) and attaching aperture (23b) may also be located in different locations that allow attaching extension (23a) and attaching aperture (23b) to interact in a similar manner which is to connect the upper portion (21a) and lower portion (21b). Preferably upper and lower portions (21a and 21b) are removably attached or pivot where adjoined to allow for easier storage. Upper and lower portions (21a and 21b) may also be part of a singular piece where attachment of the two sections in not necessary.

Figure 14:
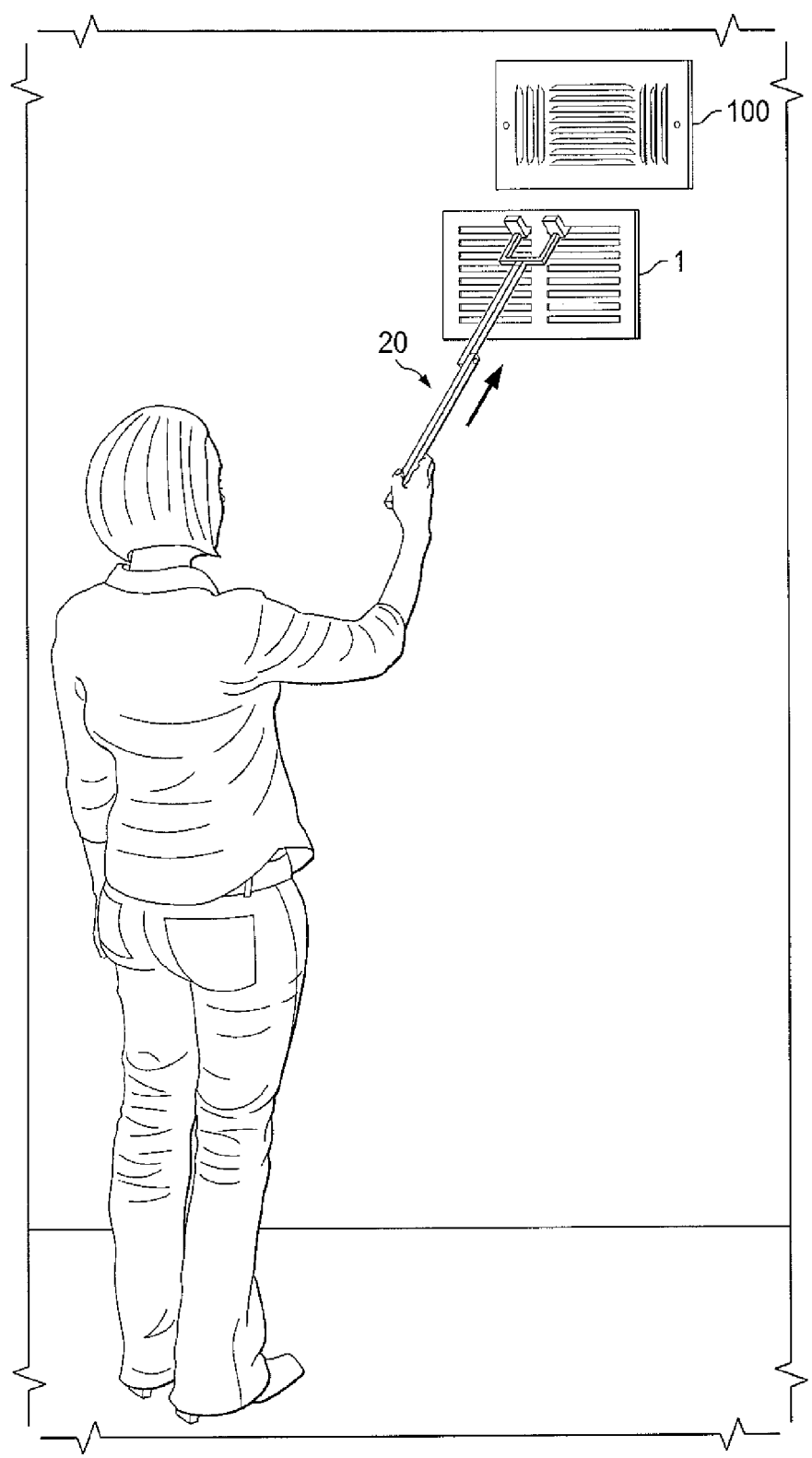
FIG. 14 is an illustrative environmental view of a user applying the invention to an airflow register.

As shown in FIG. 13 and FIG. 14 is an environmental view that illustrates an example of the whole system of the invention. In this example, a user who is unable to reach the airflow register (100) may utilize the accessory aide (20) to help with attachment and detachment of the airflow register accessory (1) to and from the airflow register (100). The user will insert the holding extension supports (27) into the vent openings (10) so that holding extension support platforms (27a) extend through the vent openings (10) with the top edge of vent openings (10) resting thereon. The holding section 25 is coupled to the holding extension supports 27 by the support arm extensions 26.

Holding extension support backings (27b) keep the airflow register accessory from sliding down the accessory aide (20). The outer side (12) of the accessory (1) may rest adjacent to the holding extension support backings (27b). The user may then extend out their arms, while holding the accessory aide (20), out towards the airflow register. The user will continue to extend out until the accessory (1), which is resting on the holding extension supports (27), attaches to the airflow register (100).

The user may also utilize the accessory aide (20) to help remove the airflow register accessory (1) from the airflow register (100). The holding extension supports (27) are inserted into the vent openings (10) as described above so that holding extension support platforms (27a) extend through the vent openings (10) with the top edge of vent openings (10) resting thereon. The user will then raise or lower the accessory aide (20) until the applied pressure of the holding extension supports (27) pushing against the airflow register (100) causes the fastening means (3) to release its grip and detach airflow register accessory (1) from the airflow register (100).

The accessory may be made in a plethora of decorative finishes thus allowing a user to easily change the décor in a room. Alternatively, the accessory may mimic the finish of the airflow register to which it is attached. Preferably, the accessory is made from a light-weight material such as a plastic or a metal.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention.

Having described the invention, we claim:

1. An airflow accessory, comprising:
a first airflow register accessory body structure having an outer surface being situated proximate to the area being ventilated, an inner surface, a plurality of elongated ledges, each of said plurality of ledges being located proximate to a plurality of ventilation opening apertures that allow for substantially unobstructed air flow to be channeled there through, said first airflow register accessory body structure capable of being placed on an exterior surface of an air register vent so that air flowing through the air register vent will be filtered for particulate removal and scented with a first desired scent;
a fastening mechanism that removably couples said airflow register accessory body structure to said air register vent, said inner surface of said airflow register accessory body structure being substantially situated near said exterior surface of said air register vent, said airflow register accessory body structure being mobile to be removed and replaced when said first desired scent is depleted;
one or more of said plurality of ledges on said first airflow register accessory body structure supporting a scented gel composition impregnated with a predetermined fragrance, said impregnated fragrance being activated when a sheet coating surrounding the gel composition is removed to be air-activated, said gel composition proximate to said ventilation opening apertures on the first airflow register accessory body structure, and said scented gel composition being located on each of said plurality of ledges substantially across an entire surface area of the air register vent, said fragrance being emitted into the air flow channeled through the air register vent and apertures in the first airflow register accessory body structure, said scented gel composition does not substantially obstruct the air flow through the first airflow register accessory body structure,
said scented gel composition having a diluent of water in the range of 30% to 50% by weight of the gel composition, a polymeric gel in the range of 50% to 70% by weight of the gel composition, a scented fragrance component in the range of 0.75% to 3.75% by weight of the gel composition, a colorant of 0.05% to 2.75% by weight of the gel composition, and an antimicrobial additive with range of 0.20% to 5% by weight of the gel composition.

2. The airflow accessory of claim 1, wherein said fastening mechanism is a magnet.

3. The airflow accessory of claim 1, wherein said fastening mechanism is magnetic tape strip.

4. The airflow accessory of claim 1, wherein said fastening mechanism is an adhesively secured magnetic tape strip.

5. The airflow accessory of claim 1, wherein said scented gel composition is an oil-based composition having impregnated fragrance.

6. The airflow accessory of claim 1, wherein said scented gel is a water-based composition having a scented aroma.

7. The airflow accessory of claim 1, wherein said scented gel is placed into scented fabric.

8. The airflow accessory of claim 1, wherein said scented gel is placed into scented fabric,
a first airflow register accessory body structure having an outer surface being substantially situated proximate to the area being ventilated, an inner surface, a plurality of elongated ledges, each of said plurality of elongated ledges being located proximate to a plurality of ventilation opening apertures that allow for substantially unobstructed air flow to be channeled there through, said first airflow register accessory body structure capable of being placed on an exterior surface of an air register vent and said first airflow register accessory body is configured to be of a similar shape as the shape of the air register vent so that air flowing through said air register vent will be filtered for particulate removal and scented with a first desired scent;
a fastening mechanism that removably couples said airflow register accessory body structure to said air register vent, said inner surface of said first airflow register accessory body structure being substantially situated near said exterior surface of said air register vent, said first airflow register accessory body structure being mobile to be removed and replaced when scent is depleted;
one or more of said plurality of elongated ledges on said first airflow register accessory body supporting a scented gel composition impregnated with a predetermined fragrance, said impregnated fragrance being activated when a sheet coating surrounding the scented gel composition is removed to be air-activated,
said scented gel composition coupled proximate to said ventilation opening apertures and located on each of said plurality of elongated ledges of the first airflow register accessory body structure substantially across an entire width of the air register vent, said fragrance being emitted into the air flow channeled through the air register vent and apertures in the first airflow register accessory body structure, said scented gel composition does not substantially obstruct the air flow through the first airflow register accessory body structure,
said scented gel composition having a diluent of water in the range of 30% to 50% by weight of the gel composition, a polymeric gel in the range of 50% to 70% by weight of the gel composition, a scented fragrance component in the range of 0.75% to 3.75% by weight of the gel composition, a colorant of 0.05% to 2.75% by weight of the gel composition, and an antimicrobial additive with range of 0.20% to 5% by weight of the gel composition.

9. The airflow accessory of claim 8, wherein said fastening mechanism is a magnet.

10. The airflow accessory of claim 8, wherein said fastening mechanism is a magnetic tape strip.

11. The airflow accessory of claim 8, wherein said fastening mechanism is an adhesively secured magnetic tape strip.

12. The airflow accessory of claim 8, wherein said scented gel composition is an oil-based composition having impregnated fragrance.

13. The airflow accessory of claim 8, wherein said scented gel is a water-based composition having a scented aroma.

14. A method of provided fragrance to airflow channeled through an air register vent, comprising the steps of:
providing a first airflow register accessory body structure having an outer surface being substantially proximate to the area being ventilated, an inner surface, a plurality of elongated ledges, each of said plurality of elongated ledges being located proximate to a plurality of ventilation opening apertures that allow for substantially unobstructed air flow to be channeled there through,
placing said first airflow register accessory body structure on an exterior surface of said air register vent, said airflow register accessory body is configured to be of a similar shape as the shape of the air register vent so that air flowing through the air register vent will be filtered for particulate removal and scented with a first desired scent;
fastening said first airflow register accessory body structure to said air register vent, said inner surface of said first airflow register accessory body structure being substantially situated near said exterior surface of said air register vent, said first airflow register accessory body structure being mobile to be removed and replaced when scent is depleted;
supporting a scented gel composition, impregnated with a predetermined fragrance, on each of said plurality of elongated ledges substantially across an entire surface area of said air register vent said impregnated fragrance being activated when a sheet coating surrounding the gel composition is removed to be air-activated, said gel composition being positioned proximate to said ventilation opening apertures on the first airflow register accessory body structure,
emitting said fragrance into the air flow channeled through the air register vent and apertures in the first airflow register accessory body structure, said scented gel composition does not substantially obstruct the air flow through the first airflow register accessory body structure,
said scented gel composition having a diluent of water in the range of 30% to 50% by weight of the gel composition, a polymeric gel in the range of 50% to 70% by weight of the gel composition, a scented fragrance component in the range of 0.75% to 3.75% by weight of the gel composition, a colorant of 0.05% to 2.75% by weight of the gel composition, and an antimicrobial additive with range of 0.20% to 5% by weight of the gel composition.

15. The method of claim 14, wherein said fastening step is accomplished with a magnet.

16. The method of claim 14, wherein said fastening step is accomplished with a magnetic strip tape.

17. The method of claim 14, wherein said fastening step is accomplished with an adhesively secured magnetic tape strip.

18. The method of claim 14, wherein said scented gel composition is an oil-based composition having impregnated fragrance.

19. The method of claim 14, wherein said scented gel is a water-based composition having a scented aroma.

20. The method of claim 14, wherein said scented gel is placed into scented fabric.

21. The method of claim 14, where said fastening step is performed using a connector.

* * * * *

UNITED STATES PATENT AND TRADEMARK OFFICE
CERTIFICATE OF CORRECTION

PATENT NO.         : 9,726,395 B2
APPLICATION NO.    : 13/843232
DATED              : August 8, 2017
INVENTOR(S)        : Scott David Hammer It is certified that error appears in the above-identified patent and that said Letters Patent is hereby corrected as shown below:

Claim 8, Lines 1-2 (Column 11, Lines 8-9), replace "The airflow accessory of claim 1, wherein said scented gel is placed into scented fabric," with --An airflow accessory, comprising:--

Signed and Sealed this
Twenty-sixth Day of June, 2018

Andrei Iancu
*Director of the United States Patent and Trademark Office*